United States Patent
Lin et al.

(10) Patent No.: US 9,594,021 B2
(45) Date of Patent: Mar. 14, 2017

(54) APPARATUS OF DETECTING TRANSMITTANCE OF TRENCH ON INFRARED-TRANSMITTABLE MATERIAL AND METHOD THEREOF

(71) Applicant: National Applied Research Laboratories, Taipei (TW)

(72) Inventors: Chun-Fu Lin, Taichung (TW);
Chun-Li Chang, Chiayi County (TW);
Tai-Shan Liao, Hsinchu (TW);
Hung-Ji Huang, Hsinchu (TW);
Chi-Hung Huang, Hsinchu (TW)

(73) Assignee: NATIONAL APPLIED RESEARCH LABORATORIES, Taipei (TW)

( * ) Notice: Subject to any disclaimer, the term of this patent is extended or adjusted under 35 U.S.C. 154(b) by 59 days.

(21) Appl. No.: 14/824,187

(22) Filed: Aug. 12, 2015

(65) Prior Publication Data
US 2017/0045448 A1    Feb. 16, 2017

(51) Int. Cl.
*G01N 21/00* (2006.01)
*G01N 21/86* (2006.01)
*G01N 21/88* (2006.01)
*G01N 21/59* (2006.01)

(52) U.S. Cl.
CPC ......... *G01N 21/59* (2013.01); *G01N 2201/12* (2013.01)

(58) Field of Classification Search
CPC .... G01N 21/59; G01N 21/25; G01N 21/5911; G01N 2201/12

USPC ............... 356/432, 237.4, 237.3, 237.5; 250/559.51, 559.45

See application file for complete search history.

(56) References Cited

U.S. PATENT DOCUMENTS

| | | | |
|---|---|---|---|
| 5,436,464 A * | 7/1995 | Hayano | G01N 21/94 250/225 |
| 8,643,833 B1 * | 2/2014 | Hung | G01N 21/9501 356/237.1 |
| 2002/0088952 A1 * | 7/2002 | Rao | G01N 21/9501 250/559.45 |
| 2002/0171825 A1 * | 11/2002 | Krantz | G01N 21/95607 356/237.1 |
| 2008/0211109 A1 * | 9/2008 | Kumagai | G01N 21/9501 257/774 |
| 2014/0072204 A1 * | 3/2014 | Minekawa | G01N 23/225 382/149 |
| 2014/0226223 A1 * | 8/2014 | Bremer | G02B 7/182 359/811 |

* cited by examiner

*Primary Examiner* — Sunghee Y Gray
(74) *Attorney, Agent, or Firm* — Jackson IPG PLLC; Demian K. Jackson

(57) ABSTRACT

An apparatus is provided for detecting transmittance of a trench. The trench is located on an infrared-transmittable material, which can be a wafer. The wafer is obtained after a ditching process. An image of the wafer is fetched. The contrast of the image is greatly enhanced. The contrast-enhanced image is used for automated analysis of the transmittance of the trench. Accuracy of detecting the transmittance is improved. Hence, the present invention uses a simple structure to detect transmittance defects of the trench for ensuring goodness of the wafer.

8 Claims, 2 Drawing Sheets

APPARATUS OF DETECTING TRANSMITTANCE OF TRENCH ON INFRARED-TRANSMITTABLE MATERIAL AND METHOD THEREOF

TECHNICAL FIELD OF THE INVENTION

The present invention relates to detecting transmittance of trench; more particularly, relates to detecting transmittance of a trench on a wafer obtained after a ditching process, where contrast of an image of the wafer is greatly enhanced for detection; automatic infrared analysis of transmittance of the trench is processed with the contrast-enhanced image; accuracy of detecting the transmittance of the trench is improved; and transmittance defects of the trench are detected for ensuring goodness of the wafer.

DESCRIPTION OF THE RELATED ARTS

During packaging an integrated circuit (IC) wafer and testing its function, defect detection devices are provided for the wafer before being diced, while few devices are provided for the wafer obtained after being diced. In fact, because the blade speed and ditching depth are hard to control, the following two situations may happen after the wafer is ditched:

First, the ditching force may not be big enough. After ditching out a street on the wafer, defects of non-cut-through areas may appear. These defects would result in broken dies in the following process of die bonding.

Second, the ditching force may be excessive. After ditching out the street, areas near the street on the back of the die may be cracked.

Although these two types of defects formed after ditching the wafer can be effectively detected through scanning electron microscopy (SEM) before dicing the wafer, this kind of traditional detection is expensive and takes time. Hence, it is not suitable for on-line detection and is hard to be automated. An optical device for photographing the wafer under a visible light is another choice for detection. A pure visible light source is shone on the wafer to detect a street; and, then, a light intensity sensor is used to receive the visible light reflected by the wafer. Any area in the street having worse transmittance than a normal street would obtain a stronger energy of the light reflected and be identified as a defect. However, the color of the wafer ditching tape and the capability of light transmission would have serious impacts on the result of the transmission detection. Consequently, the method of using the optical device for photographing the wafer under a visible light would obtain an image having bad contrast and the transmission of the trench is hard to be detected. In fact, the transmission detection of trench is usually done artificially. Yet, artificial detection has shortcomings of high labor cost and low detection efficiency. Moreover, misjudgments may happen to the staff on operating the detection due to lack of experience or eyestrain.

Accordingly, for ditching a wafer of an infrared-transmittable material, a ditching blade would form a trench by ditching the infrared-transmittable wafer. But, the factors of blade type, ditching speed, the blade-rotating velocity and the ditching tape will affect the quality of the trench. Therein, the transmittance of the trench especially and seriously affects the ditching of the wafer. Hence, the prior arts do not fulfill all users' requests on actual use.

SUMMARY OF THE INVENTION

The main purpose of the present invention is to detect transmittance of a trench on a wafer, where contrast of an image of the wafer is greatly enhanced for detection; automatic infrared analysis of transmittance of the trench is processed with the contrast-enhanced image; and accuracy of detecting the transmittance of the trench is improved.

Another purpose of the present invention is to provide a simple structure to detect transmittance defects of the trench for ensuring goodness of the wafer.

To achieve the above purposes, the present invention is an apparatus of detecting transmittance of a trench on an infrared-transmittable material and a method thereof, where the apparatus comprises a light source, an adjustable fixing support, a light intensity sensor and a trench-transmittance analysis unit; the light source emits a visible light and an infrared light to be projected onto an infrared-transmittable material having a trench; the fixing support has an end located on a base and another end connected to the light source; the fixing support controls the light source shining on the infrared-transmittable material at an angle; the light intensity sensor is set at a corresponding direction of the same side to the light source and is located at a right angle to the infrared-transmittable material; the light intensity sensor collects bands of a light reflected by the infrared-transmittable material to obtain information of intensity of the light reflected; the analysis unit is connected with the light intensity sensor; the analysis unit has an image pre-processing; the analysis unit detects crack defects and transmittance of the trench after defining a street area; the analysis unit receives the information of intensity of the light reflected to obtain information of the transmittance of the trench; and the analysis unit classifies the infrared-transmittable material by the crack defects and the transmittance of the trench detected. Accordingly, a novel apparatus of detecting transmittance of a trench on an infrared-transmittable material is obtained.

BRIEF DESCRIPTION OF THE DRAWINGS

The present invention will be better understood from the following detailed description of the preferred embodiment according to the present invention, taken in conjunction with the accompanying drawings, in which.

DESCRIPTION OF THE PREFERRED EMBODIMENT

The following description of the preferred embodiment is provided to understand the features and the structures of the present invention.

Figure 1:
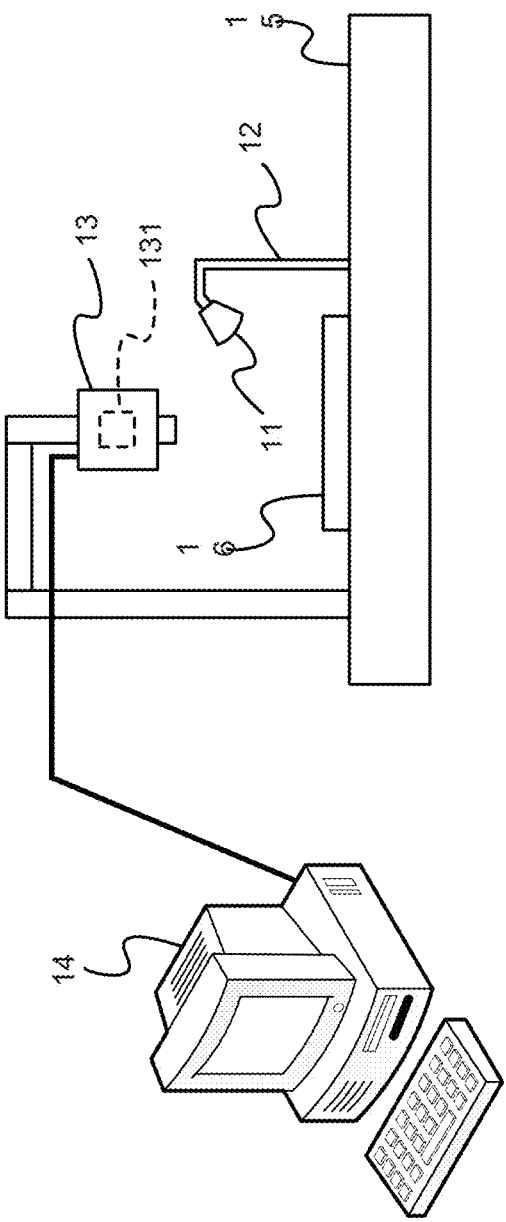
FIG. 1 is the view showing the preferred embodiment according to the present invention.
Figure 2:
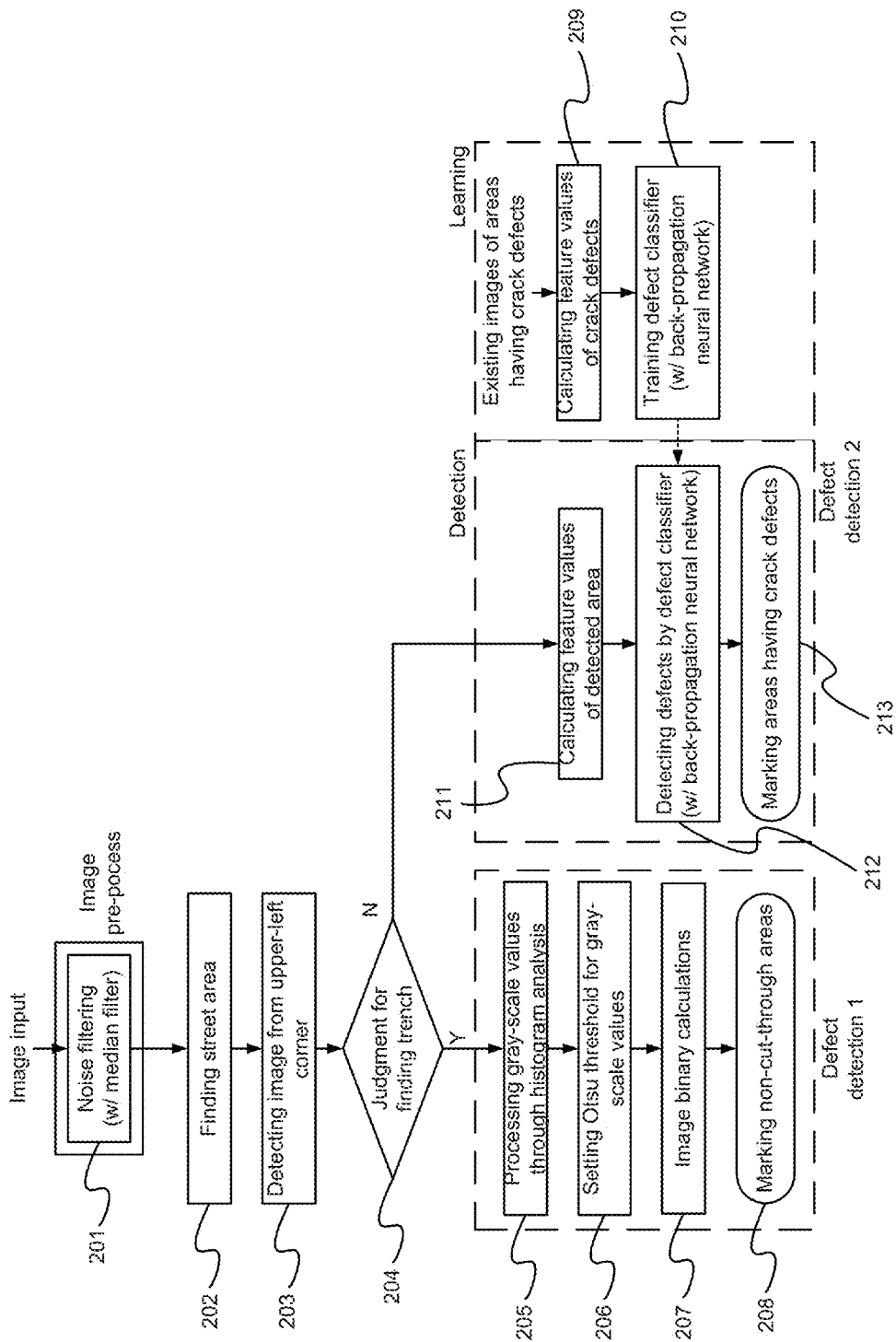
FIG. 2 is the view showing the method using the preferred embodiment.

Please refer to FIG. 1 and FIG. 2, which are a view showing a preferred embodiment according to the present invention; and a view showing a method using the preferred embodiment. As shown in the figures, the present invention is an apparatus of detecting transmittance of a trench on an infrared-transmittable material and a method thereof. As shown in FIG. 1, the apparatus comprises a light source 11, an adjustable fixing support 12, a light intensity sensor 13, and a trench-transmittance analysis unit 14.

The light source 11 emits a visible light and an infrared light to be projected onto a wafer 16 having a trench obtained after ditching.

The adjustable fixing support 12 has an end set on a base and another end connected to the light source 11 to control the light source 11 shining on the wafer 16 at an angle.

The light intensity sensor 13 is a camera to be set at a corresponding direction of the same side to the light source 11 and located at a right angle to the wafer 16. The light intensity sensor 13 has a sensing device 131 collecting bands of a light reflected by the wafer 16 to obtain information of intensity of the light reflected. The information of intensity of the light reflected are sent to the analysis unit 14.

The analysis unit 14 is connected to the light intensity sensor 13. The analysis unit 14 preprocesses an image of the wafer 16. The analysis unit 14 detects crack defects and transmittance of the trench according to the received information of intensity of the light reflected after defining a street area. Thus, the wafer 16 is classified as a good product when no crack defects and areas having poor transmittance in the street area are found.

The light source 11 on a base 15 is a halogen lamp having a cup-shaped shade, which emits a visible light with an infrared light having a wide range of wavelengths and a layer of reflector (e.g. aluminum film) is covered on an inner surface of the shade. The light source 11 is diagonally put above the wafer 16 about 45 degrees. The light intensity sensor 13 is placed at a corresponding direction of the same side to the light source 11 and located at a right angle to the wafer 16. On using the present invention, the light source 11, which emits the visible light with the infrared light having the wide range of wavelengths, shines on the wafer 16. Along the trench of the wafer 16, although non-cut-through parts of the trench allows a range of wavelength (1200 nanometers (nm)~1600 nm) of the infrared light to be transmitted, other wavelengths of the infrared light (850~1200 nm and wavelengths above 1600 nm) and the visible light (400~700 nm) would be reflected. The reflected part of the infrared light in the light source 11 is enforced through the aluminum film. Thus, energy of the infrared light in the light source 11 is enforced to form stronger energy for reflected light, including the visible light with the enforced infrared light having a wide range of wavelengths, on the non-cut-through parts than that of cut-through parts on the trench of the wafer 16. Coordinated with the light sensor 13 for receiving corresponding band of light, image contrast is greatly enhanced on showing the image of the trench by the sensing device 131. In the preprocessing of the analysis unit 14, a median filter is used to preprocess the information of the transmittance of the trench. Result of the preprocessing is used to define the street area for detecting the crack defects and the transmittance of the trench. Therein, the transmittance of the trench is detected by processing the preprocessed image of the trench through histogram analysis with a transmittance threshold to be further processed through image binary calculations while candidate areas having poor transmittance are analyzed to mark areas having poor transmittance. For detecting the crack defects, a defect classifier is trained through a back-propagation neural network to define the crack defects with detected features and conditions of the crack defects inputted to the defect classifier. A wafer 16 is classified as a good product by not finding crack defects and areas having poor transmittance in the street area.

The steps for detecting the crack defects and the transmittance of the trench are shown in FIG. 2 as follows:

In step 201, an image of the wafer 16 is obtained from the sensing device 131 to be inputted into the analysis unit 14 for filtering noises with a median filter. In step 202, a location of the street area is found. In step 203, the part of the image containing the street area is detected from the upper-left corner. Then, in step 204, a judgment for finding a trench is processed. If a trench is found, a judgment for deciding the transmittance of the trench is processed. At first, in step 205, gray-scale values of the detected area are processed through histogram analysis. Then, in step 206, an Otsu threshold is set for the gray-scale values to find the non-cut-through areas in the trench. In step 207, image binary calculations are processed. At last, in step 208, the non-cut-through areas are marked to identify areas having poor transmittance. Thus, defects of poor trench transmittance are detected.

In step 204, if no trench is found, detection for finding crack defects is processed. At first, in step 209, defect learning is processed. Existing images of areas having crack defects are inputted for training to calculate feature values of crack defects. Then, in step 210, the defect classifier is trained through a back-propagation neural network; and, in step 212, a result is sent. On detecting crack defects, in step 211, feature values of the detected area are calculated and, in step 212, another result is sent. By receiving the above two results, the defect classifier is used to detect crack defect. At last, in step 213, areas having crack defects are marked to find out poor conditions of the crack defects. Thus, crack defects are detected.

The present invention is mainly used to detect transmittance of a trench of an infrared-transmittable wafer obtained after a ditching process. The present invention greatly enhances contrast of image of the wafer for detection; processes automatic infrared analysis of the transmittance of the trench with the contrast-enhanced image; and accuracy of detecting the transmittance of the trench is improved. Hence, the present invention uses a simple structure to detect transmittance defects of the trench for ensuring goodness of the wafer.

To sum up, the present invention is an apparatus of detecting transmittance of a trench on an infrared-transmittable material and a method thereof, where contrast of an image of a wafer obtained after a ditching process is greatly enhanced for detection; automatic infrared analysis of transmittance of a trench of the wafer is processed with the contrast-enhanced image; accuracy of detecting the transmittance of the trench is improved; and transmittance defects of the trench are detected for ensuring goodness of the wafer.

The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. An apparatus of detecting transmittance of a trench on an infrared-transmittable material, comprising
   a light source emitting a visible light and an infrared light projected onto an infrared-transmittable material having a trench cut therein such that first wavelengths of the infrared light are transmitted in non-cut-through portions of the trench and second wavelengths above and below the first wavelengths are reflected by the trench;
   an adjustable fixing support having an end located on a base and another end connected to said light source, said fixing support controlling an incidence angle of said light source shining on said infrared-transmittable material;
   a light intensity sensor located at a corresponding direction of the same side to said light source and being located at a right angle to said infrared-transmittable material, said light intensity sensor collecting bands of a light reflected by said infrared-transmittable material to obtain information of intensity of said light reflected; and a trench-transmittance analysis unit connected with said light intensity sensor, preprocessing an image of said light reflected from the infrared-transmittable material, detecting crack defects and transmittance of said trench after defining a street area bounding the trench, receiving said information of intensity of said light reflected to obtain information of said transmittance of said trench, and classifying said infrared-transmittable material by said crack defects and said transmittance of said trench detected.

2. The apparatus according to claim 1, wherein said infrared-transmittable material is a wafer obtained after being ditched.

3. The apparatus according to claim 1, wherein said light source is a halogen lamp having a cup-shaped shade and a layer of an aluminum-film reflector is covered on an inner surface of said shade.

4. The apparatus according to claim 1, wherein said light intensity sensor is a camera; said camera has a sensing device to sense energy of said light reflected by said trench of said infrared-transmittable material; and said light intensity sensor sends information of said energy to said analysis unit.

5. The apparatus according to claim 1, wherein said light reflected comprises a visible light of wavelength of 400~700 nanometers (nm) and an infrared light of wavelength of 850~1200 nm and wavelength greater than 1600 nm.

6. The apparatus according to claim 1, wherein said image is preprocessed by using a median filter to obtain said information of said transmittance of said trench to detect said crack defects and said transmittance of said trench after defining said street area.

7. The apparatus according to claim 1, wherein said analysis unit detects said transmittance of said trench by processing said preprocessed image of said trench through histogram analysis with a transmittance threshold to be further processed through image binary calculations while candidate areas having poor transmittance are analyzed to identify areas having poor transmittance.

8. The apparatus according to claim 1, wherein said analysis unit trains a defect classifier through a back-propagation neural network; wherein said defect classifier defines said crack defects with detected features and conditions of said crack defects inputted to said defect classifier; and wherein said infrared-transmittable material is classified as a good product by not finding crack defects and areas having poor transmittance in said street area.

* * * * *